US00PP08583P

United States Patent [19]

Zaiger et al.

[11] Patent Number: Plant 8,583

[45] Date of Patent: Feb. 8, 1994

[54] PLUM TREE "EARLIQUEEN"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 45,021

[22] Filed: Apr. 12, 1993

[51] Int. Cl.[5] ..... A01H 5/00

[52] U.S. Cl. ..... Plt./38.1

[58] Field of Search ..... Plt. 38.1

*Primary Examiner*—James R. Feyrer

[57] ABSTRACT

A new and distinct variety of plum tree which has the following outstanding features that are desirable in a new variety.

1. Early maturity of large fruit.
2. Fruit with good flavor and eating quality.
3. Heavy and regular production.
4. Vigorous upright growth.
5. Fruit with an attractive bordeaux red skin color.
6. Fruit with firm flesh, good handling and shipping quality.
7. The ability of the fruit to stay firm on the tree 6 to 10 days after shipping ripe.

1 Drawing Sheet

ORIGIN OF THE VARIETY

The present new variety of plum tree originated from seeds collected from an open pollinated seedling with the field identification number 61EC540. The selected seedling 61EC540 was selected from seedlings that were grown from seeds of a plum tree of unknown parentage. A large group of these seedlings were grown and maintained under close observation by us and one such seedling, which is the present variety, being especially desirable with respect to its fruit was selected for asexual reproduction and commercialization.

ASEXUAL REPRODUCTION OF THE VARIETY

The present new variety of plum tree was asexually reproduced by budding, as performed by us in our experimental orchard located near Modesto, Calif., such reproductions show that all characteristics are established and transmitted through succeeding propagations and run true to the original tree in all respects.

SUMMARY OF THE VARIETY

The present new variety of plum tree which is of large size, vigorous upright in growth and a regular and productive bearer of large, yellow flesh, clingstone fruit with good flavor and eating quality. The fruit is further characterized by having early maturity, a high degree of attractive wine red skin color, good handling and shipping quality and in comparison to the early maturing Red Beaut Plum (U.S. Plant Pat. No. 2,539) the new variety has heavier production with larger, more uniform size fruit and is approximately 2 days later in maturity.

PHOTOGRAPH OF THE VARIETY

The accompanying photographic reproduction in color are of typical specimens of the foliage and fruit of the present new variety of plum tree. The illustrations of the upper and lower surface of the leaves are shown with the exterior and a sectional view of the fruit being divided in its suture plane to show flesh coloration and a stone remaining in place. The photographic illustrations were taken shortly after being pick at maturity (shipping ripe) and the colors are as nearly true as is reasonably possible in a color representation of this type.

DESCRIPTION OF THE VARIETY

The following is a detailed botanical description of the new and distinct variety of plum tree, its flowers, foliage and fruit, as based on observations of specimens grown near Modesto, Calif. with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium.
- *Bearer.*—Regular.
- *Production.*—Productive.

Trunk:
- *Size.*—Large.
- *Texture.*—Medium shaggy.
- *Color.*—Brown to dark brown (6-F-6) to (6-F-8).

Branches:
- *Size.*—Medium.
- *Texture.*—Medium rough.
- *Lenticels.*—Medium number. Medium to large size.

Leaves:
- *Size.*—Medium. Average length — 4" to 4¼". Average width — 1" to 1⅜".
- *Margin.*—Finely serrate.
- *Form.*—Oblanceolate — pointed.
- *Texture.*—Smooth.
- *Glands.*—Globose. Medium size. Number varies from 0 to 3. Average number 2. Positioned on base of leaf blade and upper portion of petiole.
- *Petiole.*—Size — medium. Medium length. Medium thickness.
- *Color.*—Upper surface — yellow green to green (28-D-8) to (28-E-8). Lower surface — light green to grayish green (28-D-4) to (28-D-6).

Flower buds:
- *Size.*—Medium.
- *Length.*—Medium.

Flowers:

*Blooming period.*—Feb. 22, 1992 to Mar. 1, 1992. Varies slightly due to weather conditions.

*Pollen.*—Present.

*Color.*—White.

*Size.*—Medium.

Fruit:

*Maturity when described.*—Firm ripe.

*Date of first picking.*—May 25, 1992.

*Date of last picking.*—Jun. 2, 1992.

*Size.*—Large. Comparatively uniform. Average diameter axially — 2¼" to 2½". Average transversely in suture plane — 2⅜" to 2⅞".

*Form.*—Nearly globose, slightly flattened at base and apex.

*Suture.*—Shallow, extends from base to apex.

*Ventral surface.*—Nearly round.

*Cavity.*—Rounded to slightly elongated in suture plane. Average depth — ⅜". Average breadth — ½".

*Apex.*—Varies from slight pistil point to slight depression.

*Base.*—Retuse.

Skin:

*Thickness.*—Medium.

*Texture.*—Medium — tenacious to flesh.

*Tendency to crack.*—None.

*Bloom.*—Moderate.

*Down.*—Wanting.

*Color.*—Garnet red to Bordeaux red (10-D-8) to (11-D-8) when shipping ripe. If left on tree 6 to 10 days after shipping ripe the color becomes a maroonish blue black.

Flesh:

*Texture.*—Firm.

*Juice.*—Moderate.

*Ripens.*—Evenly.

*Fibers.*—Small, tender.

*Aroma.*—Very little.

*Flavor.*—Good — mild, good balance between acid and sugar.

*Eating quality.*—Good.

*Color.*—Yellowish white to pale yellow (4-A-2) to (4-A-3).

Stone:

*Type.*—Clingstone.

*Size.*—Medium to large. Average length — 1 1/16". Average width — 1". Average thickness — ½".

*Form.*—Obovate.

*Apex.*—Cuspidate.

*Base.*—Varies from straight to round.

*Sides.*—Nearly equal.

*Surface.*—Pitted throughout.

*Tendency to split.*—None.

*Color.*—Indian yellow to light tan (5-B-5) to (5-B-7).

Use:

*Market.*—Local and long distance. Dessert.

Storage quality: Good.

Shipping quality: Good.

The new plum tree, its foliage, flowers and fruit herein described may vary in slight detail due to climatic, soil conditions and cultural practices under which the variety may be grown. The present description is that of the variety grown under the ecological conditions prevailing near Modesto, Calif.

We claim:

1. A new and distinct variety of plum tree, substantially as illustrated and described, characterized by its large size, vigorous, upright growth and a productive and regular bearer of early maturing, large, firm, clingstone fruit with good flavor and eating quality; the new variety is further characterized in comparison to the early maturing Red Beaut Plum (U.S. Plant Pat. No. 2,539) as producing larger fruit, being heavier in production and the fruit being approximately 2 days later in maturity.

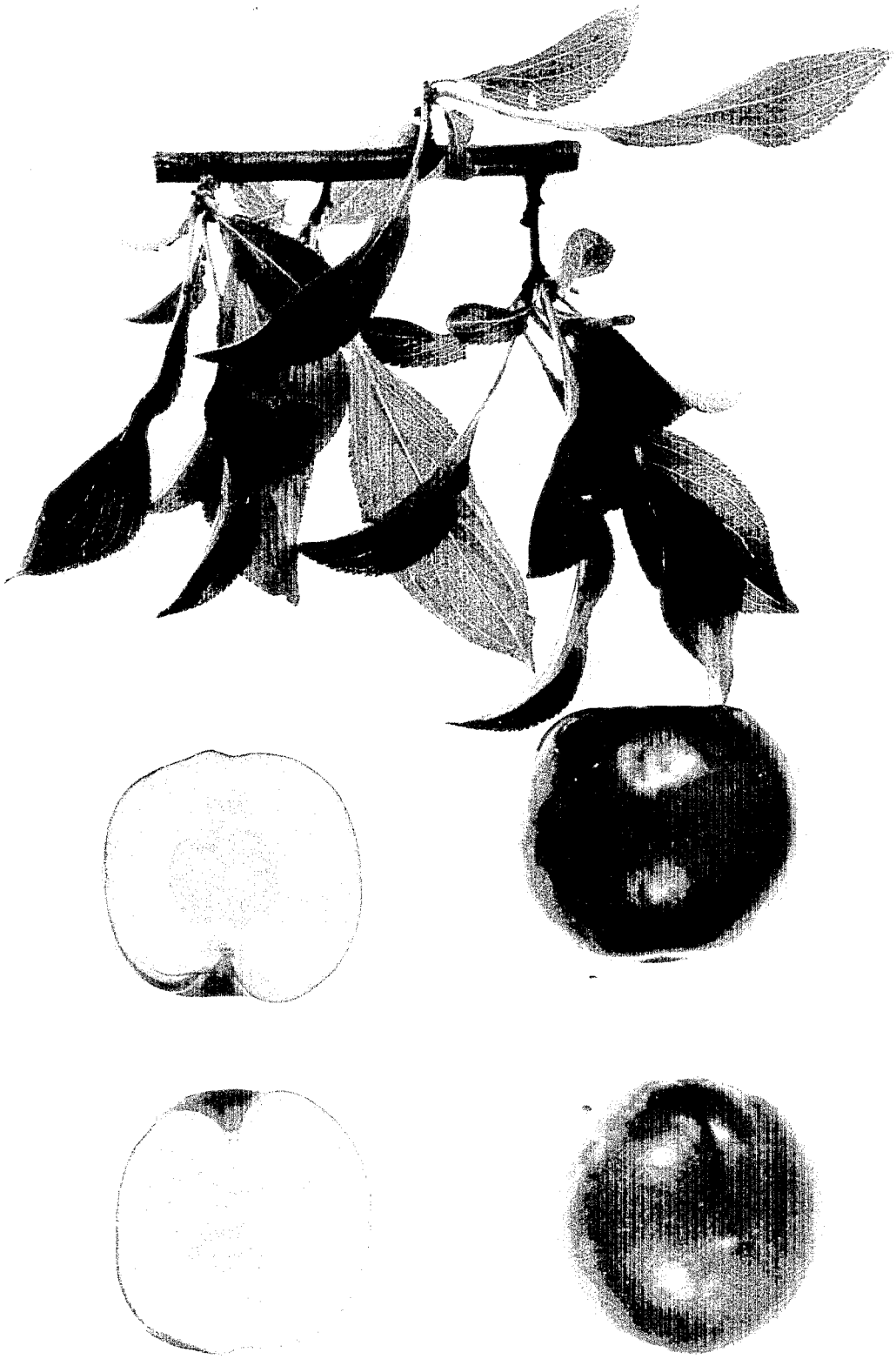

* * * * *